(12) United States Patent
Ten Eyck et al.

(10) Patent No.: US 7,966,678 B2
(45) Date of Patent: Jun. 28, 2011

(54) INFANT CARE BED WITH EVALUATION CAPABILITIES

(75) Inventors: Lawrence G. Ten Eyck, Ellicott City, MD (US); Richard Smith, Clarksville, MD (US)

(73) Assignee: General Electric Company, Schenectady, NY (US)

( * ) Notice: Subject to any disclaimer, the term of this patent is extended or adjusted under 35 U.S.C. 154(b) by 339 days.

(21) Appl. No.: 11/295,862

(22) Filed: Dec. 7, 2005

(65) Prior Publication Data
US 2007/0129612 A1    Jun. 7, 2007

(51) Int. Cl.
  *A47B 13/00*  (2006.01)
(52) U.S. Cl. .................. 5/603; 5/600; 600/301
(58) Field of Classification Search .............. 600/22, 600/300, 301; 128/903–905, 920; 5/600, 5/603, 655; 177/44
See application file for complete search history.

(56) References Cited

U.S. PATENT DOCUMENTS

| | | | |
|---|---|---|---|
| 5,840,019 A * | 11/1998 | Wirebaugh | 600/300 |
| 6,109,100 A * | 8/2000 | Buckley et al. | 73/198 |
| 6,409,654 B1 | 6/2002 | McClain | |
| 7,038,588 B2 * | 5/2006 | Boone et al. | 340/573.1 |
| 2002/0196141 A1 | 12/2002 | Boone et al. | |
| 2003/0135087 A1 * | 7/2003 | Hickle et al. | 600/26 |
| 2005/0085687 A1 | 4/2005 | Mackin et al. | |
| 2005/0215844 A1 | 9/2005 | Ten Eyck et al. | |
| 2007/0167691 A1 * | 7/2007 | Causevic | 600/301 |

FOREIGN PATENT DOCUMENTS
WO    WO99/13766    3/1999

* cited by examiner

*Primary Examiner* — Henry M Johnson, III
*Assistant Examiner* — Kai Rajan
(74) *Attorney, Agent, or Firm* — Roger M. Rathbun

(57) ABSTRACT

An infant care bed for supporting an infant having incorporated therein, certain testing and evaluation devices to carrying out the evaluation of an infant in a medical care facility. The apparatus can carry out at least one of the following tests on the infant: determining the weight of an infant, determining the sucking strength of an infant, determining the ability of the infant to hear certain frequencies and determining the bilirubin level of the infant's blood. The infant care bed includes a computer with a memory device such that the hospital can input a customized protocol of the tests to be performed on the infant and the criteria for passing the tests. A data input allows the personnel to input test results and a display provides an account of the tests performed and the tests not performed to assure that all of the tests required by the protocol are conducted.

15 Claims, 1 Drawing Sheet

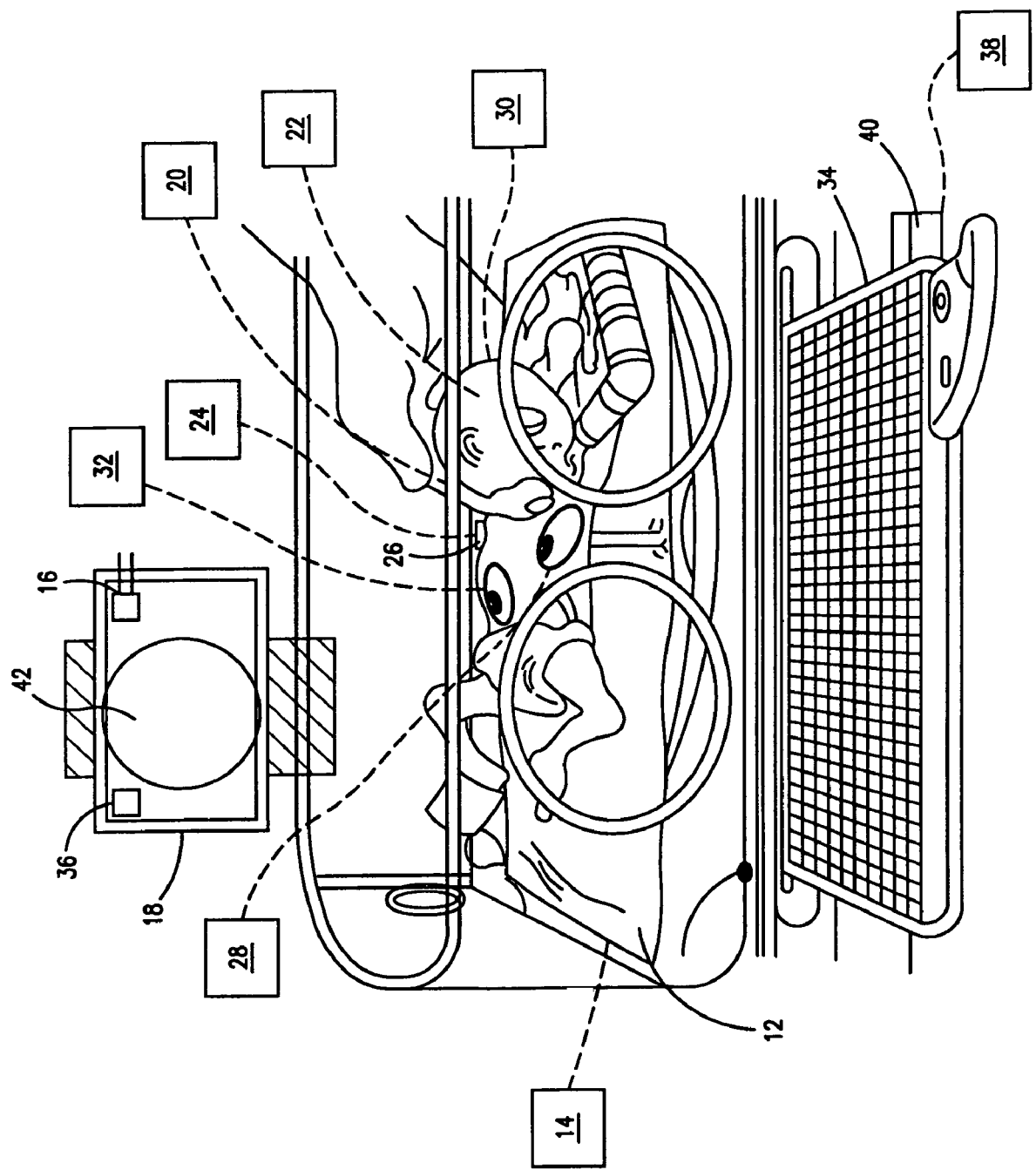

INFANT CARE BED WITH EVALUATION CAPABILITIES

BACKGROUND

The present invention relates to an infant care bed and, more particularly, to an infant care bed having various devices associated therewith to carry out the evaluation of an infant and to utilize a test protocol to carry out the conducting of certain tests on the infant.

In the care of newborn infants, the infant is normally birthed in a labor and delivery room and the infant is initially provided with warmth and other care while in that room. One piece of infant care apparatus that is commonly used in the labor and delivery room is an infant care bed which basically provides a flat platform on which the infant rests so that the caregiver can carry out various evaluations and tests on the infant to determine its wellbeing.

With respect to such evaluations, there are a number of tests or examinations that are performed on the infant and, at the present, the devices for carrying out those tests either for admitting the infant or to assure that the infant is sufficiently stable and well to be discharged from the facility are generally located in various areas of the hospital and therefore the caregiver must seek out the necessary testing devices to conduct the needed tests. Such common tests include at least one of evaluating the infant's weight, the sucking intensity of the infant, the hearing ability of the infant at differing frequencies and an evaluation of the level of bilirubin in the blood of the infant.

Also, within each hospital, the staff may have different tests to be conducted on the infant and different criteria to successfully judge the test results in order to pass those tests. As such, with different care personnel attending to the infant, there is the possibility that one or more of the desired tests can be inadvertently omitted or not carried out in the manner established by the hospital.

In the normal course of the hospital stay, the various tests and evaluations, including the tests enumerated above, are preformed at various times and by the use of individual devices that sense and determine the desired information and there is no single infant care apparatus that is capable of attending to all of the criteria determined in evaluating the infant in order to qualify that infant for admission and/or discharge from the hospital facility.

Accordingly, it would therefore be advantageous to have an infant care bed that has available, certain of the equipment used in the evaluation of the infant so that the caregiver can readily and conveniently carry out the tests on that infant by the use of one apparatus and not need to bring the testing devices from other locations or move the infant from one location to another in order to complete the testing and evaluation of that infant. In addition, it would be advantageous to have an infant bed that could provide a means to insure that all of the tests desired to be carried out by a particular hospital were carried out on the infant in a consistent and thorough manner.

It would be further advantageous to have a infant care bed having the facility for the hospital to enter a protocol listing the various tests that the hospital wants to be carried out on the infant in an evaluation thereof, and have an input device to enable the caregiver to input data of the test results and to further have a display device that shows the check list for the inputted test protocol advising of the completed tests and the tests yet to be administered to the infant.

SUMMARY OF THE INVENTION

Accordingly, the present invention relates to an infant care bed that has incorporated thereinto, various equipment and devices used in carrying out an evaluation of an infant so that the equipment and devices are readily available to the caregiver at a single location at the infant care bed.

Those tests that have been heretofore described are carried out by the use of the following devices: the weight evaluation is, of course, carried out by a scale, the sucking strength is determined by means of a pressure sensor that can sense the pressure at the infant's mouth, a hearing evaluation is carried out by means of a hearing monitor that ascertains the ability of the infant to hear at various predetermined frequencies and a bilirubin evaluation is conducted by a bilirubinometer that detects the bilirubin level in the blood of the infant.

With the present invention, therefore, all of those basic tests, common to the admission as well as the discharge of an infant are incorporated into the present infant apparatus. By "incorporated into" it is meant that the particular piece of equipment or device is physically affixed to or built into the infant care apparatus and is not easily removed. Thus, a caregiver utilizing the present infant care bed can be assured that all of the devices necessary to carry out the common tests conducted on an infant during an admission or a discharge are always available at the infant care bed and that a caregiver has not removed a device that is necessary to carry out the common tests.

The infant care bed also has a computer memory and a central processing unit so that the hospital can input, or have programmed by the manufacturer, its own customized test protocol into the infant care bed to enable the caregiver to follow a hospital originated protocol to effectively ensure that all of the tests required by the hospital for a particular purpose i.e. admission or discharge, are conducted as well as to verify that the results of those tests meet or exceed the standards established by that hospital.

Thus, the hospital itself can determine what tests it wants to perform on an infant for the particular purpose and can enter that protocol into the computer memory so that the caregiver will know what tests are required. The bed also has an input that is accessible to the caregiver, and who can input the tests that have been given to the infant and the test results. As such, the computer memory can keep a continuous record of the tests performed on each infant to assure the hospital that all of the tests required by the hospital are performed on the infant and meet a particular hospital standard and the results of those tests are readily available in electronic form to the caregiver at any time and at the site where the infant is located.

Since all of the tests are listed on the inputted protocol, the bed has a display device that enables the user to ascertain what tests have been completed, the test results for those completed tests and a list of the tests yet to be performed to meet the hospital protocol standards.

In an embodiment, the electronic test results in the memory of the infant bed can be transmitted by wires or wireless means to an electronic medical record (EMR) that is centrally located within the hospital facility. Thus, all of the testing of an infant can be carried out by a dedicated infant care bed that the caregiver can be assured has the necessary devices to carry out that testing and the data can be inputted electronically and available at that infant care bed for the particular infant and/or sent to a central location to be entered and stored in the patient's electronic medical record along with the records of other patients.

Thus with the present invention, all of the devices necessary to carry out certain evaluations of an infant are present at one location and that location also has all of the test data for the infant and a check list of the tests required by that particular hospital to be carried out in that evaluation of the infant.

These and other features and advantages of the present invention will become more readily apparent during the following detailed description taken in conjunction with the drawings herein.

BRIEF DESCRIPTION OF THE DRAWINGS

FIG. 1 is a schematic view of an infant care bed constructed in accordance with the present invention.

DETAILED DESCRIPTION OF THE INVENTION

Referring now to the Figure, there is shown a schematic view of an infant care bed 10 of the present invention. As can be seen, there are a number of devices that are incorporated into the infant care bed 10 that are present in order for the caregiver to carry out certain tests on an infant that can be positioned atop of the infant platform 12.

Accordingly, since the basic devices are readily available commercially in stand-alone form, some are shown schematically in the FIGURE and which include a scale 14 that, as shown, can be inserted underneath the infant to take the weight of the infant, however, the scale can be more permanently located beneath the infant and such embodiments are readily available commercially. A readout 16 for the weight of the infant as determined by the scale 14 is mounted to a monitor housing 18 to be visually read by the caregiver, however the readout, as well as the infant scale itself, can be any variety of device that is capable of determining the weight of an infant being attended to on the infant care bed 10 and communicating that weight to a caregiver or directly inputting that information to a memory device of a computer. The infant scale can be as shown and described in U.S. Pat. No. 5,376,761, issued Dec. 27, 1994 U.S. and entitled "In Bed Infant Scale".

As another device described aforesaid, there can be a pressure sensor 20, such as a manometer, that receives a pressure signal from some device that communicates with the mouth of an infant and the pressure sensor 20 therefore can sense the sucking intensity or strength of the infant and which is an indication of the infant's ability to take nourishment. Again, the pressure sensor 20 is shown schematically since such devices are current available commercially, however, in the present invention, the pressure sensor 20 is attached to or is a built-in component of the infant care bed 10.

There may also be a hearing monitor 22 that determines the ability of the infant to hear at various frequencies and which is also incorporated into the infant care bed 10 for easy access by the caregiver. Again, the hearing monitor 22 can be any device to carry out the hearing test and several are currently available commercially as stand-along devices. The present hearing monitor 22 is, as explained, either attached to or built into the infant care bed 10.

Finally, as a further basic testing device of the present infant care bed 10, there is a bilirubinometer 24 that has a probe 26 that attaches to the infant in order to sense the bilirubin concentration in the blood of the infant. As with the other testing devices, the bilirubinometer 24 is a commercially available device and is attached to or built into the infant care bed 10.

While all of these devices alone can be conventional devices currently and readily available, with the present invention, they are incorporated into the infant care bed 10 so that they cannot be easily removed from the infant care bed 10 to be taken to and used at another location and thus the caregiver is assured that the basic tests, whether for the purpose of admitting or discharging the infant, can be carried out by the use of the present infant care bed 10.

As has now been described, the basic infant care bed 10 has all of the basic devices to carry out tests on an infant that are used in the admission or discharge of the infant at a health care facility, that is, there is incorporated into the infant care bed 10 sufficient devices to carry out at least one of the following tests on the infant; sucking strength, hearing ability, bilirubin concentration in the blood stream and weight and those are the basic tests common to such admission or discharge. All of the devices are therefore attached to or built into the infant care bed 10 so that the caregiver can be assured that those devices are present in order to carry out the basic tests on the infant at one location where the infant is located resting on the infant platform 12 of the infant care bed 10.

In addition to the basic tests of the infant, there are also other test devices used on an infant that can be incorporated into the present infant care bed 10 that are of use to the caregiver and one or more are more applicable to either the admission process or the discharge process, but not necessarily both.

As such, the present infant care bed 10 may also include, as other desired tests, further devices incorporated into the infant care bed 10 and which can include blood oxygenation, again through the use of the oximeter 28 as well as blood pressure by means of a blood pressure device 30, skin temperature by a thermometer 32 as well as developmental tests, motor tests and other physical observations, including APGAR tests, pH tests, arterial blood gases and acid base deficit.

The result of all of the above-identified tests as well as other tests that may be desired to be performed on the infant can all be inputted by means of an input device 34 such as a keyboard so the results of any and all tests performed on an infant being attended to on the infant care bed 10 can be electronically recorded by the caregiver by the input device 34. Such other tests include, but are not limited by, blood gas analysis, respiratory rate, development assessment, temperature stability, physical assessment, stool and voiding pattern, CBC, blood culture, ultrasound and other tests, all of which provide results in the form of data and information that can be inputted by means of the input device 34.

All of the inputted data and information can be transmitted to a central data storage facility 36 along with the other information and data concerning the infant, such as name, history and the like. That central data storage facility 36 can be located, as shown, in the infant care bed 10 so that all of the relevant information and data concerning the particular infant is present and accessible to the caregiver at the infant care bed 10. The information and data can also be transmitted, either by wire or wireless means, to a further remote central storage center 38 located in the hospital facility so that the information and data relating to that infant can be retained along with information and data with respect to other infants being cared for at the hospital facility. A wireless transmitting unit 40 is illustrated in the FIGURE.

The central data storage facility 36 also includes a system to input or enter a test protocol that sets forth all of the tests required by the particular hospital to be administered to an infant being cared for on the infant care bed 10. The test protocol can be inputted by the input device 34 by use of the keyboard or may be entered by the use of a floppy disc or CD-ROM or other input means that can be utilized and which transfers the test protocol to the central data storage facility 36.

The test protocol itself can be established by the particular hospital and which provides a listing of all of the tests required by that hospital for a particular purpose, that is, there may be a test protocol inputted for the admission of an infant and a different test protocol established for discharge of that infant. In either instance, the caregiver can have a listing of the particular tests for the specific purpose to be performed on the infant and, as those tests are administered by the caregiver, the data is inputted by means of the input device 34 and that test can be considered completed when the results are achieved an inputted to the central data storage facility 36.

In that manner, the caregiver is constantly reminded as to the total number of tests that need to be performed on the infant and can have a visual display 42 so that the caregiver is advised of the tests that have be completed as well as the test that have yet to be performed in order to complete the test protocol.

The test protocol can be written by the individual hospital in order to serve its needs as to the tests to be carried out on an infant or can be inputted by the manufacturer of the infant care bed 10 in accordance with the desire of the hospital, however in either case, the hospital can customize the test protocol in accordance with the particular requirements of that hospital and a test protocol of one hospital may very well differ from the test protocol of another hospital.

Accordingly, as can now be seen, the infant care bed 10 of the present invention has incorporated therein certain testing devices having the ability to carry out various tests on an infant so that the testing devices necessary to conduct the tests are available at one location on the infant care bed. Also available at that same infant care bed is a programmed test protocol so that the caregiver can be advised of all of the tests to be performed on an infant and, as the tests are carried out, the caregiver can input the test results at the infant care bed and a central data storage facility can maintain the test results and provide a display to the caregiver advising of the completed tests as well as notice of the tests remaining on the test protocol that have yet to be performed. All of the above functions are, therefore, available at a single location convenient to the caregiver to assure that the full range of desired tests are carried out on each infant.

Those skilled in the art will readily recognize numerous adaptations and modifications which can be made to the infant care bed of the present invention which will result in an improvement in the evaluation of an infant in a hospital facility, yet all of which will fall within the scope and spirit of the present invention as defined in the following claims. Accordingly, the invention is to be limited only by the following claims and their equivalents.

What is claimed is:

1. An open infant care bed, said infant care bed comprising a base having an infant platform on which an infant is adapted to be positioned, said infant care bed having incorporated therein evaluation devices including a scale for determining the weight of an infant, a pressure sensor for determining the sucking strength of an infant, a hearing monitor for determining the ability of the infant to hear certain frequencies and a bilirubinometer for determining the bilirubin level in the blood of an infant, the infant care bed having a central processing unit (CPU) and a memory device having stored therein an electronic protocol of a plurality of evaluation tests to be performed by the evaluation devices on an infant positioned on the infant platform and a manual input device for a caregiver to input data indicative of tests performed by a caregiver on an infant, the infant care bed further having an electronic display, the CPU adapted to send the manually inputted data by the caregiver and the listing of the evaluation tests stored in the memory device including at least one of weight, sucking strength, hearing ability and bilirubin level to the electronic display to visually indicate to a user the completion of any of such tests.

2. The infant care bed as defined in claim 1 wherein the input device is a keyboard.

3. The infant care apparatus as defined in claim 1 wherein the infant care bed further includes one of an oximeter, a blood pressure monitor and a skin temperature sensor for determining the body temperature of an infant.

4. The infant care apparatus as defined in claim 1 wherein the infant care bed includes a transmitting unit for transmitting data from the memory device by wireless transmission to a remote location.

5. A method of carrying out an evaluation of an infant in a health care facility, said method comprising the steps of:
providing an open infant care bed having a device for determining the weight of an infant, a device for determining the sucking strength of the infant, a device for determining the hearing ability of the infant and a device for determining the bilirubin concentration in the blood of an infant, each of said devices producing test results indicative of the determined parameter,
providing a central processing unit (CPU) and a memory device in the infant bed,
inputting a protocol of a plurality of tests desired to be conducted on an infant into the memory device, including weight, sucking strength, hearing ability and bilirubin concentration in the infant's blood to the memory device,
manually inputting the test results for the tests performed by a caregiver on an infant set forth in the protocol of tests,
using the CPU to send the protocol of plurality of tests and the inputted test results to a display device to display which inputted tests have been completed and which inputted tests have not been completed.

6. The method as defined in claim 5 wherein the method further comprises the step of transmitting the data and information from the at least two devices by means of a transmitting unit to a remote location to be stored in the infant's electronic medical record.

7. The method as defined in claim 6 wherein the step of transmitting the data and information comprises transmitting the data and information by wireless transmission.

8. The method as defined in claim 5 wherein the step of providing at least one device comprises further providing at least one device of the following: an oximeter, a blood pressure monitor and a temperature sensor for determining the body temperature of an infant.

9. An open infant bed for use in the evaluation of an infant at a health care facility, said infant bed having incorporated therein, the following evaluation devices:
a weighing device for determining the weight of an infant and provide signals indicative of an infant's weight;
a pressure sensor device communicating with the mouth of an infant for determining the sucking strength of an infant and provide signals indicative of the sucking strength of an infant,
a hearing device for determining the ability of the infant to hear certain frequencies and provide signal indicative of the hearing of an infant, and
a bilirubinometer device for determining the bilirubin level in the blood of an infant and provide signals indicative of the level of bilirubin in the blood of an infant,
the infant bed further having a central processing unit (CPU) and a memory device having stored therein, a protocol of a plurality of tests required by the health care facility in carrying out the evaluation of the infant using one or more of the evaluation devices, the plurality of tests including weight, sucking strength, hearing ability and bilirubin level, a manual input device to enable a caregiver to manually input and record the results of tests indicative of the infant weight, sucking strength, hearing and bilirubin level in the blood of the infant that have been preformed on the infant by the caregiver; and a display device, the CPU adapted to send the protocol of the plurality of tests stored in the memory device and the input by the caregiver into the manual input device to the display device to provide a visual display of the tests listed on the protocol and the test results that have been inputted by the caregiver.

10. The infant bed as defined in claim 9 wherein the infant bed further has a transmitting device to transmit data from the memory device to a remote location.

11. The infant bed as defined in claim 10 wherein said transmitting device transmits the data by wireless transmission.

12. The infant bed as defined in claim 9 further includes an input device to electronically input the protocol of the plurality of tests to the memory device.

13. The infant bed as defined in claim 12 wherein the input device is a keyboard.

14. The infant bed as defined in claim 12 wherein the input device is adapted to input the protocol of tests into the memory device.

15. The infant bed as defined in claim 12 wherein the infant care bed further includes one of an oximeter, a blood pressure monitor and a skin temperature sensor.

* * * * *